United States Patent
Nilsson

(10) Patent No.: US 9,207,227 B2
(45) Date of Patent: Dec. 8, 2015

(54) COMPOSITION OF MULTIPHASE FLOW

(75) Inventor: Carl Nilsson, Haugesund (NO)

(73) Assignee: Polytec, Haugesund (NO)

( * ) Notice: Subject to any disclaimer, the term of this patent is extended or adjusted under 35 U.S.C. 154(b) by 625 days.

(21) Appl. No.: 13/511,050

(22) PCT Filed: Nov. 17, 2010

(86) PCT No.: PCT/EP2010/067637
§ 371 (c)(1),
(2), (4) Date: Sep. 25, 2012

(87) PCT Pub. No.: WO2011/061210
PCT Pub. Date: May 26, 2011

(65) Prior Publication Data
US 2013/0008235 A1  Jan. 10, 2013

(30) Foreign Application Priority Data
Nov. 23, 2009  (NO) .................................. 20093393

(51) Int. Cl.
*G01N 33/28* (2006.01)

(52) U.S. Cl.
CPC .................................. *G01N 33/2823* (2013.01)

(58) Field of Classification Search
CPC ....................................................... G01N 33/28
USPC .................. 73/53.05, 61.43, 861.04, 863.02, 73/863.03; 166/250.01, 264
See application file for complete search history.

(56) References Cited

U.S. PATENT DOCUMENTS

| | | | |
|---|---|---|---|
| 4,815,536 A | | 3/1989 | Prendergast et al. |
| 5,415,024 A | * | 5/1995 | Proffitt et al. ................. 73/61.44 |
| 5,763,794 A | * | 6/1998 | Marrelli ...................... 73/863.02 |
| 6,546,809 B1 | | 4/2003 | Andreussi |
| 7,469,597 B2 | * | 12/2008 | Flaten et al. ................ 73/861.07 |
| 2008/0295607 A1 | * | 12/2008 | Di Maggio et al. ......... 73/861.04 |
| 2009/0139345 A1 | * | 6/2009 | Xie ............................. 73/861.04 |

FOREIGN PATENT DOCUMENTS

| | | |
|---|---|---|
| EP | 1291638 A2 | 3/2003 |
| WO | 9425732 A1 | 11/1994 |

OTHER PUBLICATIONS

International Search Report from PCT/EP2010/067637 dated Feb. 14, 2011 (2 pages).
Norwegian Search Report from Norwegian Application No. 20093393 dated Apr. 9, 2010 (2 pages).
International Preliminary Report on Patentability from PCT/EP2010/067637 dated Mar. 2, 2012 (4 pages).

* cited by examiner

*Primary Examiner* — Hezron E Williams
*Assistant Examiner* — Hoang Nguyen
(74) *Attorney, Agent, or Firm* — Osha Liang LLP

(57) ABSTRACT

In a method for determining a total hydrocarbon composition of a multiphase flow including gas and liquid, the method includes taking different samples of the gas and liquid at at least two different thermodynamic states of the multiphase flow. The method further includes analyzing the different samples, and using a molar balance of the different samples at the at least two different thermodynamic states to calculate a gas molar fraction and a liquid molar fraction. The gas molar fraction and liquid molar fraction may be used for deriving an overall composition of the multiphase flow and for deriving the gas and liquid volume fractions.

19 Claims, 1 Drawing Sheet

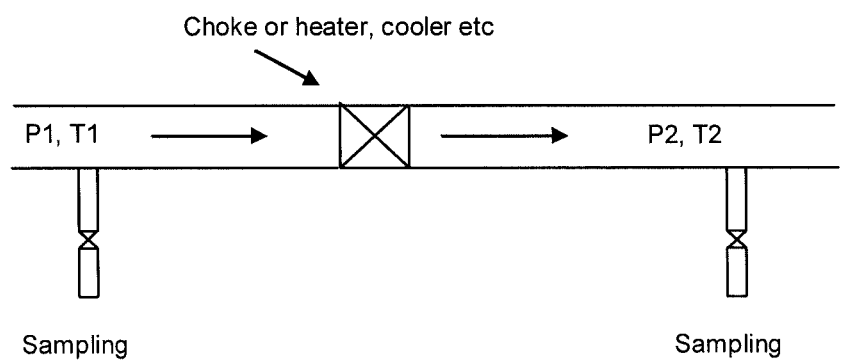

COMPOSITION OF MULTIPHASE FLOW

CROSS-REFERENCE TO RELATED APPLICATIONS

This application is a national stage application of PCT/EP2010/067637, filed on Nov. 17, 2010, entitled "Composition of Multiphase Flow," which claims priority to Norwegian Patent Application No. 20093393, filed on Nov. 23, 2009. Both PCT/EP2010/067637 and Norweigan Patent Application No. 20093393 are incorporated by reference herein in their entireties.

FIELD OF THE INVENTION

One or more embodiments of the present invention include a method for determining the total hydrocarbon composition and molar phase fractions of a multi-phase flow comprising gas and liquid, and doing so without depending on flow metering or single-phase sampling.

Further the volumetric phase fractions may be computed from the molar fractions using knowledge of the molar volumes of the phases.

BACKGROUND

Knowledge of the total hydrocarbon composition is important for several reasons. One reason is using this knowledge as input data for flow instrumentation, e.g., flow computers for wet-gas/multiphase meters.

Another reason is as input to pipeline transport capacity simulations and flow assurance. Further reasons are for optimal processing and refining, for calculating the economic value of the flow, for reservoir management, and for process troubleshooting.

The economic value of a hydrocarbon flow is directly related to the composition of the flow. The costs of transport, separation and refining the hydrocarbon flow are also determined by the composition. Thus knowing the composition as accurately as possible is an important factor for maximizing the revenue and minimizing the operational expenditure (OPEX), e.g. optimizing production, transportation, and processing for optimal regularity and profit for a given field development.

The importance of knowing the overall or total composition makes it essential to have a technique that does not depend on measurements that sometimes introduce large uncertainties.

The usual method today for finding the composition of a hydrocarbon multiphase flow is by analyzing samples of the gas and oil from points of interest in the production facility, and using flow rate information provided by gas and oil flow meters or multiphase meters to recombine the measured gas and oil compositions into the total hydrocarbon composition. The gas and oil molar volumes must also be known in order to perform this recombination.

Existing techniques are used for well testing, allocation, production and reservoir management etc. However, existing techniques has its weaknesses. Sometimes inconsistent compositions are obtained and depending on circumstances it can be difficult to pinpoint where the error is. An additional independent composition measurement would therefore be beneficial.

It is well known that flow metering is exposed to measurement errors when determining the composition and gas/oil ratio of a well-stream. The use of known methods can have large uncertainties in the flow measurements depending on the flow regime and gas/liquid fraction, water-cut etc. The accuracy of flow metering technology also depends in various degree on the flow composition and composition dependent properties like density, viscosity, permittivity etc. There is a risk that poor flow measurements are used to compute a poor composition that in turn is used in the fluid property calculations of the flow instrumentation. This may in turn lead to even poorer flow measurements.

The total composition can alternatively be obtained from bottom-hole single-phase samples, but such samples are often difficult and costly or even impossible to obtain.

Error in the composition will result in large unnecessary costs due to erroneous basis for further processing. Examples are inefficient separation and processing; inefficient use of chemicals, injection of inhibitors, de-emulsifiers etc.; poor transport capacity utilization; poor operation of multiphase flow meters, which in turn creates new processing and transport problems. In the worst case a process shutdown will be the result.

It is thus a need for an alternative or additional method for estimating the total composition of a hydrocarbon multiphase flow that does not depend on any flow instrumentation.

SUMMARY OF THE INVENTION

In general, in one aspect, one or more embodiments of the invention provide for a back-up or alternative technique for the measurement of the composition of multiphase flows, i.e. GOR or CGR that is independent of flow measurements.

In general, in one aspect, one or more embodiments of the method for measuring the total hydrocarbon composition of a multi-phase flow is independent of flow measurement and molar volumes. Hence the overall hydrocarbon composition that is found is affected by neither the uncertainties associated with the flow metering nor the uncertainty in the molar volumes. The method is further obtained with little extra effort or cost.

In short, in accordance with one or more embodiments, the total composition and GOR (gas/oil ratio) or CGR (condensate/gas ratio) is found by extending the sampling and analysis of the gas and oil to two different pressure/temperature conditions. From this extended set of individual phase compositions, the gas and oil molar fractions and hence the overall compositions is calculated. By using the molar volumes and the conversion factors of standard conditions, the GOR or CGR is can be found. In accordance with one or more embodiments, all of this is achieved without any form of flow instrumentation.

In general, in one aspect, one or more embodiments of the method uses an up to now overlooked mechanism that relates the different changes in partitioning, due to pressure/temperature changes of the flow over, for instance, a valve, of the different molecules between the gas and liquid phases to the molar conservation law for the upstream and downstream condition of the flow.

In general, in one aspect, one or more embodiments of the method will also be useful for other applications besides finding the overall composition. These include checking of multiphase/wet-gas meters accuracy by comparing GOR/CGR, providing new types of multiphase/wet-gas metering strategies, providing a new way of multiphase/wet-gas pipeline monitoring, and process-plant/refinery troubleshooting.

The ability to find the composition and GOR independent of flow measurement instrumentation also creates new practical applications.

One or more embodiments of the method may be used for exploration well testing as well as for routine composition measurement of production wells or mixed streams for allocation purposes.

In general, in one aspect, one or more embodiments of the invention include a method for determining the total hydrocarbon composition of a multi-phase flow comprising gas and liquid. The method includes sampling the gas and liquid at at least two different thermodynamic states of the multi-phase flow, analyzing the different samples, and using the molar balance of the samples at the two different thermodynamic states to calculate the gas and liquid molar fraction for deriving the overall composition of the flow.

Other aspects of the invention will be apparent from the following description and the appended claims.

BRIEF DESCRIPTION OF THE DRAWINGS

FIG. 1 shows an example of how the method may be performed in accordance with one or more embodiments of the invention.

DETAILED DESCRIPTION OF THE INVENTION

Specific embodiments of a method for determining the total hydrocarbon composition of a multi-phase flow comprising gas and liquid are described in detail with reference to the accompanying FIGURE.

In the following detailed description of embodiments, numerous specific details are set forth in order to provide a more thorough understanding of the method for determining the total hydrocarbon composition of a multi-phase flow comprising gas and liquid. However, it will be apparent to one of ordinary skill in the art that these embodiments may be practiced without these specific details. In other instances, well-known features have not been described in detail to avoid unnecessarily complicating the description.

In accordance with one or more embodiments, the first step in the method is to sample gas and liquid at two different thermodynamic states of the multi-phase flow. The liquid may comprise oil, condensate, water, or a combination of these. The two different pressure and/or temperature conditions may be produced in many different ways.

FIG. 1 shows an example of how this may be performed. Sampling points are located upstream and downstream of a device that changes the thermodynamic states of the multi-phase flow.

The device may be pressure changing means located in the path of the flow. Samples are then taken upstream and downstream of said pressure changing means. Such means may be a pressure reduction valve, a multiphase pump, venturi, orifice, or other known means. Combinations of these are also feasible.

The device may also be temperature changing means located in the path of the flow, and where said samples are taken upstream and downstream of the pressure reducing means. Such means may be a heater, a cooler or heat exchanger or a combination of these.

One or more devices changing both temperature and pressure are also feasible, for example a long pipeline. Also, a pressure reduction over a valve is normally accompanied by a temperature drop as well due to the Joule-Thomson effect.

The objective is that different samples are taken of the flow at different thermodynamic states. This may even be obtained without said means located between the sampling locations upstream and downstream of the device. The flow rate may be adjusted while taking samples at the same sampling location.

Since different flow rates will affect temperature/pressure (P,T), this will also provide the necessary samples at different thermodynamic states. An example of implementation is by changing the settings of a choke so that the sampling can be performed at the same location, either upstream or downstream the choke.

Changing pressure and/or temperature alters the way a given hydrocarbon molecule partition between the gas and liquid phases. Different molecules will change their partition in different ways, thus changing the composition of both the gas and the liquid. However, molar conservation will ensure that the overall (total) well-stream composition remains the same, since we can assume that no chemical reactions takes place in the flow.

Sampling of a multiphase flow can even be performed at the inlet and outlet of a long multiphase or wet-gas pipeline because there will be some pressure drop and temperature change between the inlet and outlet.

In general, there is no need that the fluid sampling is performed simultaneous at the two locations as long as one can assume that no significant change in the total feed (reservoir) composition between the two sampling events. Slugging will not affect the method, since there will be a well established thermodynamic equilibrium between the gas and liquid phases irrespective of the slugging.

Because the individual gas and oil compositions are known by analyzing samples at both P,T conditions one can use the molar balance to calculate the gas and oil molar fraction and thus finding the overall composition of the flow. Using the gas and oil molar volumes one can convert the molar fractions into volume fractions and the GOR or CGR using well known relationships.

It should be noted that while analyzing samples from two different thermodynamic conditions are sufficient, the method itself is easily generalized to three or more pressure/temperature conditions. In fact it is expected that the measurement accuracy will improve further by using several conditions. It is actually the usual procedure when using test separators that several (3 or 4) gas and oil sample sets are collected and analyzed. Because of the different flow rates the test separator operates at somewhat different pressures and temperatures, and thus the different sample sets are taken at different thermodynamic conditions.

Thus, in some applications it will be possible to use only a single sample point, and the necessary changes in pressure/temperature are generated by altering the flow rate.

The present disclosure has focused on measuring the hydrocarbon composition and the GOR (or CGR) since these are the most important in most applications. Mathematically, it is easy to extend the method to also measure the water molar (and volume) fraction, because there will be also partitioning between the water phase and hydrocarbon liquid and gas phase. However, the water partitioning effect is very weak unless there are very high pressures and temperatures, and the currently available analytical instrumentation is probably not accurate enough for also the water phase to be measured with satisfactory precision. The most straight forward solution to this is simply to measure the water cut in the liquid hydrocarbon phase, and then calculate the water fraction (volume and molar) from this. Operators routinely employ this water cut strategy for their multiphase meters, especially at high gas fractions (wet gas applications) and when the water content in the flow is low, <10%.

There are, in fact, various ways in which the molar fractions and total composition can be found from the analysis of the samples.

One mathematical method is described in the following where $\alpha_1$ and $\alpha_2$ are the gas molar fraction at condition 1 ($P_1$, $T_1$) and condition 2 ($P_2$, $T_2$) respectively. For two different molecules labelled by "i" and "j" with concentrations z(i) and z(j) in the total flow, it follows:

$$z(i)=\alpha_1[y_1(i)-x_1(i)]+x_1(i)=\alpha_2[y_2(i)-x_2(i)]+x_2(i) \quad (1)$$

and $$z(j)=\alpha_1[y_1(j)-x_1(j)]+x_1(j)=\alpha_2[y_2(j)-x_2(j)]+x_2(j) \quad (2)$$

where $\alpha_1$ and $\alpha_2$ denote the gas mole fractions at the two different thermodynamic conditions. The $y_1(i)$ and $y_2(i)$ are the gas phase molecular concentrations at the two conditions and in the same way the x-s represents molecular concentrations in the liquid phase.

Thus, i and j represents two different hydrocarbon molecules (for example $C_3H_8$ and i-$C_5H_{12}$), while the subscripts 1 and 2 refer to conditions 1 ($P_1$,$T_1$) and 2 ($P_2$, $T_2$). Normally one can also use analytical results for non-hydrocarbons like $N_2$, $CO_2$, $H_2S$ etc. in these equations.

Chromatography is the most common method for determining the composition. However, there are other different methods used for finding the compositions of gas, oil and water in samples taken. Among these methods are UV-VIS-IR, NMR or Raman spectroscopy, various chemical analyses (chemical composition), boiling point analyses etc. In fact, one may use any method or combination of methods that can measure the sample compositions with suitable accuracy.

Because there are two unknowns ($\alpha_1$ and $\alpha_2$) and two equations (all the different y(i) and x(i) are already measured in the gas and oil samples by GC or other suitable techniques), it is possible to solve this set of equations.

To simplify, it may be defined:

$$A_{1i}=y_1(i)-x_1(i)$$

$$A_{2i}=y_2(i)-x_2(i)$$

$$A_{1j}=y_1(j)-x_1(j)$$

$$A_{2j}=y_2(j)-x_2(j)$$

which results in:

$$\alpha_1 A_{1i}+x_1(i)=\alpha_2 A_{2i}+x_2(i) \quad (3)$$

$$\alpha_1 A_{1j}+x_1(j)=\alpha_2 A_{2j}+x_2(j) \quad (4)$$

From this, the molar fraction can be solved for:

$$\alpha_2=[\alpha_1 A_{1i}+x_1(i)-x_2(i)]/A_{2i} \quad (5)$$

$$\alpha_2=[\alpha_1 A_{1j}+x_1(j)-x_2(j)]/A_{2j} \quad (6)$$

Then, it follows that:

$$[\alpha_1 A_{1j}+x_1(j)-x_2(j)]/A_{2j}=[\alpha_1 A_{1i}+x_1(i)-x_2(i)]/A_{2i} \quad (7)$$

Finally, it can be found that:

$$\alpha_1=\{(x_{1i}-x_{2i})A_{2j}+A_{2i}(x_{2j}-x_{1j})\}/(A_{1j}A_{2i}-A_{1i}A_{2j}) \quad (8)$$

and:

$$\alpha_2=[\alpha_1 A_{1i}+x_1(i)-x_2(i)]/A_{2i} \quad (9)$$

Of course, one only needs either $\alpha_1$ or $\alpha_2$ to find the total hydrocarbon composition. When $\alpha_1$ is known, the liquid mole fraction is simply given by (1−$\alpha_1$). At $P_2$, $T_2$, the liquid mole fraction is given by (1−$\alpha_2$).

Knowing the molar volumes and the pressure and temperature, the gas molar fraction can be converted to a GOR:

$$GOR=BgV_{mg}\alpha/[V_{mo}(1-\alpha)Bo] \quad (10)$$

where $\alpha$ is the gas molar fraction at either $P_1$,$T_1$ or $P_2$,$T_2$. Because the compositions of the individual phases are known from the sample analysis, the gas and oil molar volumes ($V_{mg}$ and $V_{mo}$ for either $P_1$,$T_1$ or $P_2$,$T_2$) can be calculated by commercial PVT software or they can be measured in the PVT laboratory on the same samples.

The factors Bg and Bo converts the GOR from line conditions to standard conditions. These conversion factors can be calculated from the pressure and temperature of the flow and the known phase compositions or they can be established experimentally.

A quality check on the results will be to see that the GOR calculated at both conditions ($P_1$,$T_1$ and $P_2$,$T_2$) are approximately the same.

One should note from the above calculations that the pressure and temperature at the sampling conditions is not used at all in the calculation of the molar fractions. However, pressure and temperature measurements are needed for converting the molar fractions of the flow into volume fractions and GOR or CGR.

The procedure described above can be repeated also for other pairs of molecules. If we have analyzed the samples for N different molecules, then the molar fractions can be computed in N(N−1)/2 ways.

Normally, one will have measurements of more than 8 molecules, thus one can find the mole fractions and total composition in at least 8*7/2=28 different ways. Ideally, all these calculations will give the same results, but, in practice, there will be some deviations due to the measurement uncertainties associated with the analytical instrument(s) used for the analysis of the samples. However, taking a simple average over all results (28 or more) will give average values for the molar fractions and the total composition that is usually close to the true composition.

There is, in fact, a number of other (and non-equivalent ways) to calculate the molar fractions in addition to the one described above. For example, one can set up calculations that use 3 or 4 molecules simultaneously. The other ways of calculating the mole fractions have different sensitivities (and even different sign in the sensitivities) to the measurement uncertainties, and, by averaging over the results from several calculating techniques, one can make the final result rather insensitive to the measurement uncertainties one will typically encounter.

When heavy hydrocarbons are present in the flow, another way of calculating the phase fractions is described in the following. Heavy hydrocarbons, i.e., usually heavier than decane, C10, will not partition into the gas phase, and will thus only be measured in the liquid (oil or condensate) phase.

For a heavy molecule "n", the total concentration is given by:

$$z(n)=\alpha_1 y_1(n)+(1-\alpha_1)x_1(n)=\alpha_2 y_2(n)+(1-\alpha_2)x_2(n) \quad (11)$$

This simplifies to:

$$z(n)=(1-\alpha_1)x_1(n)=(1-\alpha_2)x_2(n) \quad (12)$$

because $y_1(n)$ and $y_2(n)$ is equal to zero, i.e., that the n-molecule has not been found in the gas samples.

Then, it can be defined:

$$P=x_1(n)/x_2(n) \quad (13)$$

It is also practical to introduce the molar liquid fractions $\beta_1=(1-\alpha_1)$ and $\beta_2=(1-\alpha_2)$.

Using equation (12) the measurements of the concentration of a heavy molecule "n" will then give the relation between the molar fluid fractions at P1,T1 and P2,T2:

$$\beta_2/\beta_1 = P = x_1(n)/x_2(n) \quad (14)$$

For a lighter molecule "i" as found in both gas and fluid, one easily calculate the fluid fractions:

$$\beta_1 = (y_1(i) - y_2(i))/[P(x_2(i) - y_2(i)) + y_1(i) - x_1(i)] \quad (15)$$

and $$\beta_2 = P\beta_1 \quad (16)$$

This calculation may be repeated with any other molecule measured in both the gas phase and the liquid phase.

The consistency of the "P" factor may be checked by using the analyses from several heavy molecules, e.g.:

$$P = x_1(C12)/x_2(C12) = x_1(C16)/x_2(C16) \text{etc.} \quad (17)$$

i.e., that the analyses of Dodecane shall give the same P-factor as, for instance, Hexadecane, etc.

This will give a check of the accuracy of P. If there is some scatter among the P-factors obtained for a number of heavy molecules (due to analytical uncertainties) one can calculate an average P-factor to use in equations (15) and (16).

Using Density Measurements and Molar Volumes

In addition to only composition analyses of the phases, one may combine this with density measurements of the individual phases for deriving the molar fractions and thus the total composition. The density measurements must be performed at the same conditions with regards to pressure and temperature as when taking samples. There exist different types of density meters on the market that may measure gas and liquid samples during very high pressure, readily more than 600 bar. An important advantage with density measurement is the high degree of accuracy possible. It is relatively easy to measure phase densities with relative uncertainties that are better than 0.05%, while composition measurements by using chromatography often has relative uncertainties between 0.2% to 4.0%.

When the "P"-factor has been found by measuring of one or more molecules that do not partition into the gas phase, one can carry out density measurements of gas- and oil samples at the two pressure and temperature conditions.

Then, the following measurements are obtained:

$\rho_{g1}$: gas density at $P_1$, $T_1$
$\rho_{g2}$: gas density at $P_2$, $T_2$
$\rho_{o1}$: gas density at $P_1$, $T_1$
$\rho_{o2}$: gas density at $P_2$, $T_2$ Measured or simulated molar volumes and mass conservations are then used to calculate the molar fractions. From mass balance, the following is obtained:

$$V_{mg1}\rho_{g1}(1-\beta_1) + V_{mo1}\rho_{o1}\beta_1 = V_{mg2}\rho_{g2}(1-\beta_2) + V_{mo2}\rho_{o2}\beta_2 \quad (18)$$

where $V_{mg1}$, $V_{mo1}$, $V_{mg2}$ and $V_{mo2}$ are the gas and oil (liquid) molar volumes at the two different thermodynamic conditions. These may be calculated from the composition of the samples using PVT software or found by direct experimental measurements.

By using equation (16), $\beta_2 = P\beta_1$ equation (18) is solved for $\beta_1$:

$$\beta_1 = (V_{mg2}\rho_{g2} - V_{mg1}\rho_{g1})/[V_{mo1}\rho_{o1} - V_{mg1}\rho_{g1} + P(V_{mg2}\rho_{g2} - V_{mo2}\rho_{o2})] \quad (19)$$

and $\beta_2$ follows from (16).

When it comes to measuring the overall composition, the traditional techniques will naturally also rely on the accuracy of the gas and oil analysis in addition to the accuracy in the flow rates and the molar volumes.

From numerical simulations, it is expected that the novel method will be more accurate than multiphase or wet gas meters in most situations for measuring the GOR and the total composition.

One or more embodiments of the present invention have several benefits. A user may for instance find the flow composition (and GOR etc) in parts of production facilities or pipeline structures where flow instrumentation like multiphase meters is absent. This will be useful for a number of process optimization or "debugging" purposes.

Another benefit of one or more embodiments of the present invention is that one can check the operation of multiphase/wet-gas meters or other flow instrumentation by comparing the derived overall composition of the flow with measurements from multiphase meters for determining the accuracy of said multiphase meters. The method may further be used for resolving process problems, optimizing a process, or for simplifying multiphase/wet-gas metering.

Further benefits of using the method of one or more embodiments of the present invention are for finding the flow composition in multiphase/wet gas pipelines for transport/flow assurance, dosing of inhibitors, processing etc, and for combining the novel technique with simple flow instrumentation like venturi meters or ultrasonic meters, for low cost but reliable wet-gas metering.

In accordance with one or more embodiments, an important benefit of one or more embodiments of the present invention is that, in most cases, depending on the number of molecules available from the sample analysis, one can calculate the molar fractions, total composition, GOR/CGR etc in a large number of different ways.

The degree of scatter amongst the different results acts as a self-verification of the results. One molecule or a group of molecules can be excluded from the calculations. This exclusion may then be examined by studying how the scattering in the results are affected. This is useful for identifying one or several molecules which are poorly analysed by analytical instrumentation.

Observing unacceptable scatter in the results shows that analytical instrument(s) used for sample analysis has poor accuracy for one, some or all of the molecules used in the calculations. If only one (or a few) of the molecules are poorly measured one can, by inspecting all results, readily identify these molecule(s) by noting the large scatter in the results where this/these molecule(s) are involved. These results can then be disregarded. It further indicates that the instrument(s) needs maintenance.

Thus, a further application of the invention in accordance with one or more embodiments is for checking the accuracy/reliability of the analytical instrumentation used in the sample analysis. An accurate instrumentation will lead to calculations that give the same or similar results for all combinations of molecules.

On the other hand, if one already knows that a given molecule is not measured accurately, for example, if its concentration is very low and close to the detection limit of the instrument, one should not include this molecule in the mole fraction calculations shown above.

There is also the possibility that by accident the denominators in equations (8) and (9) are zero or close to zero leading to divergent results. Any combination of two molecules that leads to this must be excluded.

However, it easy to set up alternative calculations, that will not involve any denominators that can "blow up". These calculations are actually more robust and attractive. The derivation leading to equations (8) and (9) has been shown here because it affords an easy way of proving the mathematical feasibility of this embodiment of the invention.

It is obvious for a man skilled in the art that the method of one or more embodiments of the present invention can be used in other industries than the oil industry. For instance, in the food industry, pharmaceutical industry, or in the paper industry where a flow of two or more phases are present.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

The invention claimed is:

1. A method for determining a total hydrocarbon composition of a multiphase flow comprising gas and liquid, the method comprising:
    taking different samples of the gas and liquid at at least two different thermodynamic states of the multiphase flow;
    analyzing the different samples; and
    using a molar balance of the different samples at the at least two different thermodynamic states to calculate a gas molar fraction and a liquid molar fraction for deriving an overall composition of the multiphase flow
    and for deriving the gas and liquid volume fractions.

2. The method according to claim 1, wherein analyzing the different samples comprises measuring chemical composition, pressure and temperature of the samples.

3. The method according to claim 2, wherein the measured pressure and temperature are used for converting the molar fractions into volume fractions and gas oil ratio (GOR) or condensate gas ratio (CGR).

4. The method according to claim 1, wherein the liquid is oil.

5. The method according to claim 1, wherein the liquid is condensate.

6. The method according to claim 1, wherein the liquid is oil, condensate, and a water phase.

7. The method according to claim 6, wherein the water phase is determined by composition.

8. The method according to claim 6, wherein the water phase is determined by water-cut sampling.

9. The method according to claim 1, wherein the at least two different thermodynamic states for the multiphase flow are obtained by altering the flow rate while taking the different samples.

10. The method according to claim 1, wherein the at least two different thermodynamic states for the multiphase flow are obtained by applying pressure changing means in the path of the flow, and wherein the different samples are taken upstream and downstream of the pressure changing means.

11. The method according to claim 10, wherein the pressure changing means is at least one of a pressure reduction valve, a multiphase pump, or a pipeline.

12. The method according to claim 1, wherein the at least two different thermodynamic states for the multiphase flow are obtained by applying temperature changing means in the path of the flow, and wherein the different samples are taken upstream and downstream of the temperature changing means.

13. The method according to claim 12, wherein the temperature changing means is at least one of a heater, a cooler or heat exchanger, or a pipeline.

14. The method according to claim 1, wherein the at least two different thermodynamic states for the multiphase flow are obtained by taking samples near an inlet and an outlet of a pipeline.

15. The method according to claim 1, wherein the derived overall composition of the multiphase flow is compared with measurements from multiphase meters for determining an accuracy of the multiphase meters.

16. The method according to claim 1, wherein the derived overall composition of the multiphase flow is used for resolving process problems, optimizing a process, or for simplifying multiphase/wet-gas metering.

17. The method according to claim 1 wherein self-verification of the method is performed by using a number of different and independent ways of calculating the molar fractions, overall composition and a GOR/CGR.

18. The method according to claim 1 wherein one molecule or a group of molecules are excluded from the calculations, and wherein the exclusion is examined by studying how a scatter in results are affected, for identifying one or several molecules which are poorly analysed by an analytical instrument, thus indicating that the instrument needs maintenance.

19. The method according to claim 17, wherein one molecule or a group of molecules are excluded from the calculations, and wherein the exclusion is examined by studying how a scatter in results are affected, for identifying one or several molecules which are poorly analysed by an analytical instrument, thus indicating that the instrument needs maintenance.

* * * * *